(12) United States Patent
Takane et al.

(10) Patent No.: US 8,335,397 B2
(45) Date of Patent: Dec. 18, 2012

(54) CHARGED PARTICLE BEAM APPARATUS

(75) Inventors: Atsushi Takane, Mito (JP); Mitsuji Ikeda, Hitachinaka (JP); Atsushi Kobaru, Hitachinaka (JP)

(73) Assignee: Hitachi High-Technologies Corporation, Tokyo (JP)

( * ) Notice: Subject to any disclaimer, the term of this patent is extended or adjusted under 35 U.S.C. 154(b) by 1019 days.

(21) Appl. No.: 12/124,666

(22) Filed: May 21, 2008

(65) Prior Publication Data
US 2008/0292199 A1  Nov. 27, 2008

(30) Foreign Application Priority Data

May 22, 2007  (JP) ................................ 2007-135916

(51) Int. Cl.
*G06K 9/40* (2006.01)
(52) U.S. Cl. ........ 382/275; 382/144; 250/307; 250/310; 250/311
(58) Field of Classification Search ........... 382/254–275
See application file for complete search history.

(56) References Cited

U.S. PATENT DOCUMENTS

| | | | | |
|---|---|---|---|---|
| 4,806,774 A * | 2/1989 | Lin et al. | ........................ | 250/550 |
| 6,021,214 A * | 2/2000 | Evans et al. | .................... | 382/141 |
| 6,465,781 B1 * | 10/2002 | Nishimura et al. | ........... | 250/306 |
| 6,571,507 B2 * | 6/2003 | Elford | ............................. | 43/21.2 |
| 6,697,507 B1 * | 2/2004 | Chapman | ...................... | 382/131 |
| 6,731,824 B2 * | 5/2004 | Russell | ......................... | 382/280 |
| 7,171,038 B2 * | 1/2007 | Adler et al. | .................... | 382/149 |
| 7,187,345 B2 * | 3/2007 | Kobaru et al. | .................. | 345/10 |
| 2002/0150303 A1 * | 10/2002 | Russell | .......................... | 382/257 |
| 2007/0057666 A1 * | 3/2007 | Shimakura et al. | ........... | 324/212 |
| 2007/0230819 A1 * | 10/2007 | Shimizu | ........................ | 382/275 |

FOREIGN PATENT DOCUMENTS

| | | |
|---|---|---|
| JP | 6-124681 A | 5/1994 |
| JP | 2003-141526 A | 5/2003 |
| JP | 2005-142038 A | 6/2005 |
| JP | 2007-59370 A | 3/2007 |

OTHER PUBLICATIONS

Japanese Office Action with partial English translation dated Dec. 6, 2011 (four (4) pages).

* cited by examiner

*Primary Examiner* — Chan S Park
*Assistant Examiner* — David Perlman
(74) *Attorney, Agent, or Firm* — Crowell & Moring LLP

(57) ABSTRACT

In a method and apparatus for removing artifacts from an image generated a charged partial beam scanning device, a scanning method is determined, and the frequency of an artifact appearing on an image can then be determined, based on scanning method. A step 703, a frequency domain for removing an artifact can be determined from the vertical and horizontal widths determined by experimentation in advance with respect to the frequency position Photography is performed to obtain an image, which is Fourier transformed and the determined frequency domain is replaced, for example, by "0." The resulting image is subjected to inverse Fourier transformation, and displayed and stored. The flow of such processing enables decreasing an artifact appearing on an image, depending on a scanning method. The frequency domain (vertical and horizontal widths) that is to be eliminated and a method for replacement by "0" are determined in advance, depending on the kind of inspected samples and a method can be selected depending on the kind of samples.

7 Claims, 5 Drawing Sheets

Actual image

Fourier transformed image 0 filling image

Inverse fourier transformed image

CHARGED PARTICLE BEAM APPARATUS

BACKGROUND OF THE INVENTION

Field of the Invention

The present invention relates to a charged particle beam apparatus and particularly relates to an image processing technique for removing artifacts generated due to the scanning method of a scan line.

When an electron beam is irradiated on a sample to be inspected, a secondary electron is generated. A scanning electron microscope obtains an observation image of the surface of a sample by the use of a phenomenon in which a secondary electron yield varies depending on the shape of the sample. Here, in general scanning electron microscopes, scanning is performed for every line in a horizontal direction within a screen, in other words, in a raster direction (a horizontal line within a screen). Lines are scanned from the top to the bottom in a perpendicular direction within a screen.

With the use of a general scanning method like this, a deviation in a perpendicular direction attributable to a charging phenomenon generated by electron beam irradiation is liable to occur, because the raster scanning is performed sequentially from the top to the bottom in a perpendicular direction within a screen. In other words, at the timing when a line is being scanned, a charge remaining on another line that has been scanned most recently affects primary and secondary electron beams during the scanning. The trajectories of the electron beams are thus altered, so a finally obtained sample image is distorted.

Japanese Patent Application Publication No. 2005-142038 discloses a technique that reduces the influence of charging in the way that the charged particle beam scans in a horizontal direction by skipping a certain number of lines in a perpendicular direction.

In addition, Japanese Patent Application Publication No. 2007-059370 (corresponding to U.S. Pat. No. 7,187,345) proposes a scanning method that involves scanning first, second and third scan lines and then scanning a plurality of scan lines between the above scan lines. Placing intervals between scan lines and thereafter scanning the intervals allows a position adjacent to the previously-scanned scan lines to be scanned after residual charge due to the previously-scanned scan lines is reduced, and thereby the accumulation of charge resulting from continuous scanning of scan lines in a same area for a short period of time can be restrained.

SUMMARY OF THE INVENTION

Japanese Patent Application Publication No. 2005-142038 discloses interlace scanning which renders it possible to decrease the accumulation of charge to some extent. However, because the time interval until the adjacent scan lines are formed is not sufficiently provided, there is a problem that the deviation of charge remains.

In addition, the proposal of Japanese Patent Application Publication No. 2007-059370 (corresponding to U.S. Pat. No. 7,187,345) makes it possible to restrain the local accumulation of charge; however, when the interval between scan lines is large, scan lines to be scanned in a position different in phase on a power-source variation curve are adjacent to each other.

A charged particle beam apparatus will be described below that is capable of restraining influences on an image caused by the accumulation of charge and the interval between scan lines sequentially scanned in time.

According to one aspect of the present invention, there is provided a charged particle beam apparatus that scans two-dimensionally a sample in a first direction with a charged particle beam so as to display an image of the scanned region with a signal based on a charged particle beam from the sample detected by the scanning, the charged particle beam apparatus employing a partitioning and interlacing method in which a plurality of partitioned regions are defined by partitioning a region to be scanned in a second direction different from the first direction, and scanning in the first direction is performed for every one of said partitioned regions sequentially in a skipping manner, wherein the charged particle beam apparatus includes an image processing section for carrying out an image processing to remove an artifact generated attributable to a scanning method of a scan line. This enables image processing of artifact removal to be filter processing for removing artifacts generated in a scanning direction and a perpendicular direction.

The above image processing section has the feature of processing the removal of the above artifacts appearing in a Fourier transformed image obtained by Fourier transforming an actual image. Specifically, when a first period is the number of pixels in each partitioned regions obtained by dividing the number of pixels in the second direction in an actual image by the number of the partitioned regions, and a frequency image is a Fourier transformed image corresponding to the first period and being obtained by Fourier transforming the actual image, the image processing section carries out a process of aligning a luminance signal of the frequency image with a "0" direction on pixels or with a background value direction on pixels arranged in the first direction at a second frequency after the Fourier transformation and corresponding to the first period.

The apparatus preferably includes a user interface for changeably setting the number of partitioned regions and an artifact removing region at least in the second direction. This enables a user to remove artifacts by scanning.

Additionally, the device may have a Fourier transforming section that Fourier transforms an actual image data and an inverse Fourier transforming section that subjects a frequency image to inverse Fourier transformation. An image Fourier transformed by the Fourier transforming section is suitable for estimating the position and width of an artifact and on the basis of this transformed image a setting value can be determined. Moreover, the Fourier transforming section may be connected to a device owned by a repair man so that a transformed image can be adjusted by monitoring.

According to another aspect of the present invention, there is provided an image processing method in a charged particle beam apparatus that scans two-dimensionally a sample in a first direction with a charged particle beam so as to display an image of the scanned region with a signal based on a charged particle beam from the sample detected by the scanning, the charged particle beam apparatus employing a partitioning and interlacing method in which scanning in the first direction is performed for partitioned regions sequentially in a skipping manner, comprising a step of defining partitioned regions by partitioning a region to be scanned in a second direction different from the first direction into a plurality of regions and a step of carrying out image processing for removing an artifact generated attributable to a scanning method of a scan line.

A program for making the above step be performed by a computer and a recording medium capable of reading such a program by a computer are also included in a category of the present invention.

According to the present invention, image processing and necessary parameters both for removing artifacts generated attributable to a scanning method are determined according to a scanning method of a scan line, whereby a fine image without artifacts can be obtained by image processing determined in advance.

DESCRIPTION OF THE PREFERRED EMBODIMENTS

This application is based on the Japanese patent application JP2007-135916, all the contents of which are incorporated in this application by reference.

Before an embodiment of the present invention is described, a former patent application (Japanese Patent Application No. 2005-221185) for reducing the influence of charge will be described. With the use of the interlace scanning method disclosed in Japanese Patent Application Publication No. 2005-142038, the former application proposes a method and an apparatus for example, in which plural scan lines are scanned after each of the first, second and third scan lines is scanned. According to this constitution, with the presence of an interval in which plural scan lines are intervened relatively between the first, second and third scan lines, the influence of the residual charge from the first scan line to the other scan lines can be restrained. In addition, during the scanning of plural scan lines relatively between the first, second and third scan lines, the charge can be decreased. Thus, it is possible to decrease the influence of absolute charge and restrain its deviation. Accordingly, based on the Japanese Patent Application Publication No. 2005-142038, and also based on the former application, the influence of charge between scan lines comes to be decreased.

Figure 2:
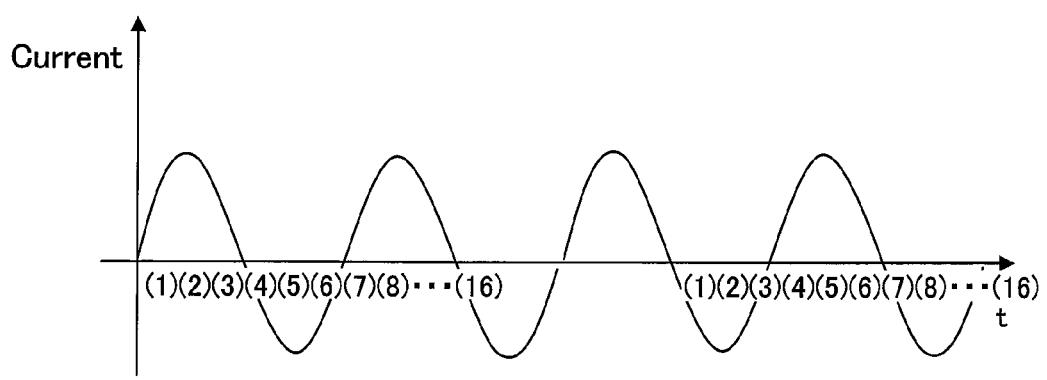
FIG. 2 is a chart indicating the relationship between the power-source variation curve and the scan line at synchronization with the power-source.
Figure 3:
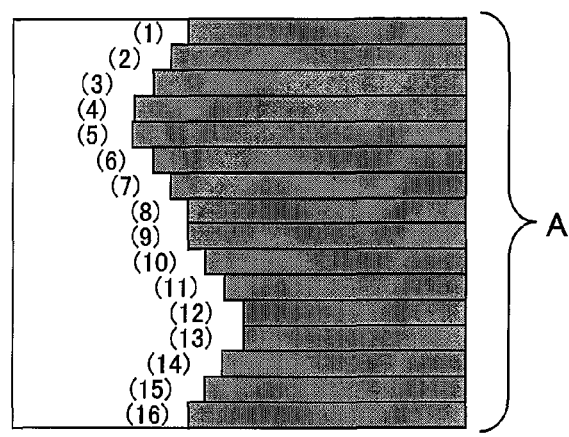
FIG. 3 is a diagram indicating a position variation example of a scan line on a screen at synchronization with the power-source.

However, depending on scanning methods of scan lines, artifacts on an image may occur in some cases. The causes in occurrence of artifacts will be described with reference to FIGS. 2 and 3. The deflection of an electron beam is influenced by the alternating magnetic field from the outside and disturbed to thereby generate blurs or artifacts on an image. In general, for the prevention of the blurs or artifacts on an image due to the alternating magnetic field, the scanning of an electron beam is synchronized with the power-source to thereby restrain the variation of an electron beam by the influence of an external alternating magnetic field. As illustrated in FIG. 2 indicated as the time (t) change of the electric current value, each of the scan lines indicated by the numbers 1 to 16 in FIG. 2 is scanned at a position having the same phase as that of a power-source variation curve varied always depending on the time t (e.g., the alternating current 50 Hz). Because of this, in an image shown in FIG. 3, as illustrated by the numbers 1 to 16, a continuous change or fluctuation occurs based on the alternating current curve in the horizontal direction of the screen depending on the scan lines. In this way, a minor fluctuation gradually but continuously generated can produce a moderate distortion in the image itself. However it is not a serious problem as the change is small. Moreover, even in a case of the signal accumulation or the like, blurs or artifacts in an image are not obtained because the signals with different phases are not accumulated.

Figure 4A:
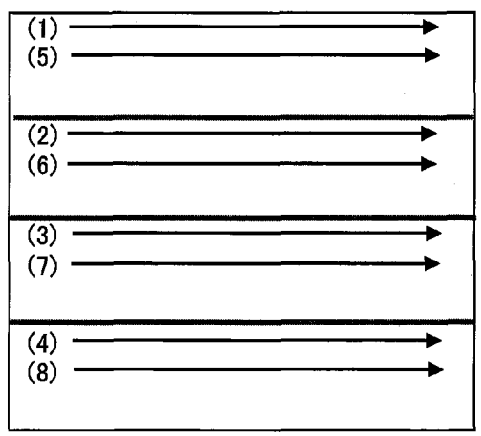
FIG. 4A is a principle diagram of a scanning method after partitioning an image into four parts for charge restraint and is also indicating a position of a scan line on an image.
Figure 4B:
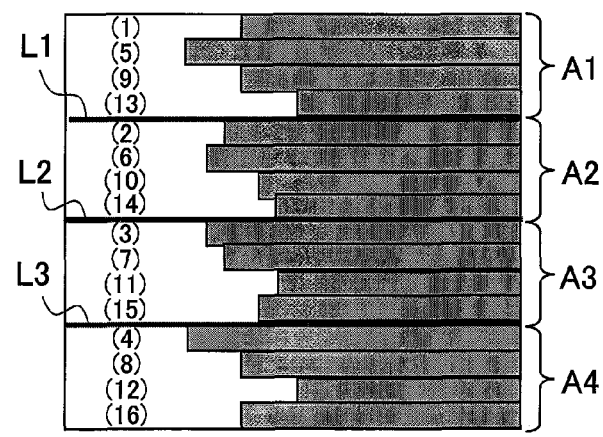
FIG. 4B is a diagram indicating an image variation example when a screen is partitioned.

As disclosed in the former patent application, the case of a scanning method will be discussed next, in which a spatial interval is placed between the first and second scan lines. As shown in FIG. 4A, a method is proposed in which an image is divided into 4 partitions in a direction perpendicular to scanning directions and scan lines are placed on each of the divided regions in turn. This method involves following steps. The partition regions A1 to A4, are defined from first to fourth regions, for example, by three lines L1 to L3 in a perpendicular direction. Then, the first to fourth scan lines are respectively placed in these first to fourth regions A1 to A4 thus partitioned. Subsequently in a similar manner, fifth to eighth scan lines are placed respectively onto the first to forth regions A1 to A4 thus partitioned. Although this method decreases the influence of charge, the change of the image becomes discontinuous as shown in FIG. 4B, which is different from the case of FIG. 3, because the scan lines scanned in positions with different phases on a power-source variation curve are adjacent. Accordingly, a new problem occurs that artifacts appear on an image attributable to the discontinuity. In an example illustrated in FIG. 4B, in particular, a large image change is generated per break of the first to fourth regions A1 to A4 thus partitioned, whereby a discontinuous change may be generated even within a partitioned region.

Now, the inventor has discussed an image processing technique for removing artifacts generated attributable to a scanning method of a scan line in the case of the former application technique.

An image processing apparatus according to one embodiment of the present invention will be set forth below with reference to the drawings.

Figure 1:
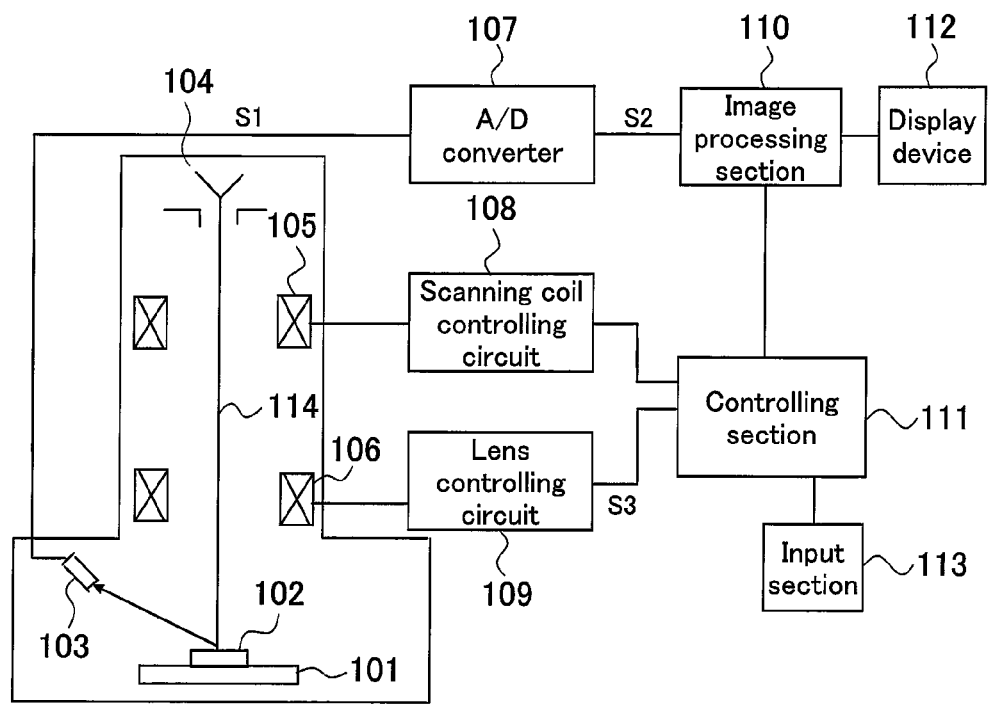
FIG. 1 is a functional block diagram indicating a schematic constitution example of a scanning electron microscope apparatus including an image processing device according to one embodiment of the present invention.

FIG. 1 is a block diagram indicating a schematic constitution example of a scanning electron microscope apparatus indicated as one example of an image processing apparatus according to one embodiment of the present invention.

As illustrated in FIG. 1, in a scanning electron microscope according to the present embodiment, 101 represents a sample stage, 102 represents a photography target sample placed on the sample stage 101, 104 represents a cathode, 105 represents a scanning coil, 106 represents an electron lens, 108 represents a scanning coil controlling circuit and 109 represents a lens controlling circuit. In the scanning electron microscope according the present embodiment, an electron beam 114 emitted from an electron source not shown is controlled so as to scan the sample 102 by the scanning coil 105; an electron generated from the sample 102 is detected with a detector 103 disposed in a reflection electron position. A signal S1 from the detector 103 is inputted into an A/D converter 107 and transformed into a digital signal S2. The digital signal S2 is inputted into an image processor 110 in which image processing and the feature quantity extraction are performed and the results are sent to a controlling section 111. In addition, the processed image is sent to be displayed on a display device 112. A focus controlling signal S3 from the controlling calculator 111 is inputted into the lens controlling circuit 109 in which the focus control can be carried out by the adjustment of the exciting current for the lens 106. Additionally, 113 is connected to the controlling section 111 and is an input section for performing a variety of scans, the input of data, and the like.

Figure 5A:
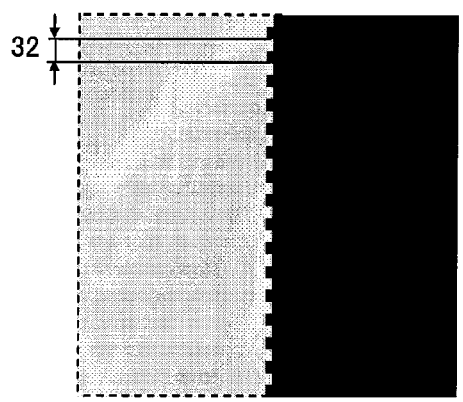
FIG. 5A is a diagram indicating an image example in which an edge is deviated at a 32-pixel period.
Figure 5B:
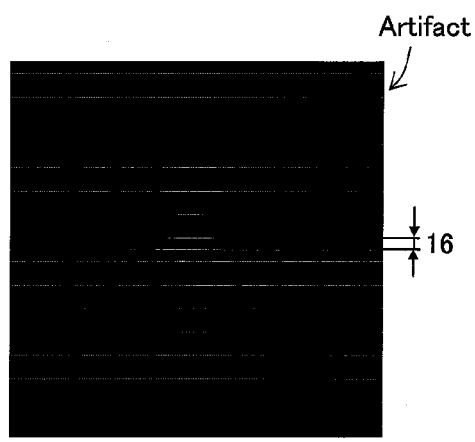
FIG. 5B is a diagram indicating an image example in which an image data indicated in FIG. 5A is Fourier transformed.

FIGS. 5A and 5B are diagrams indicating, respectively, an image example that schematizes artifacts generated by the scanning method of the former patent application and frequency properties in its image. In a scanning method as illustrated in FIG. 4A, when the number of partitions is set to be 16, a large change appearing on the image (protruded part to the left from the region of the right-hand half of FIG. 5A corresponding to the partitioned number) holds a change period (first period) per break of partitions, that is, a change period per 32 pixels in case the size of an image is 512×512 (512/16=32). The luminance change period of the edge part of FIG. 5A is 32 pixels. Here, a Fourier transformation image in which the image of FIG. 5A is Fourier transformed and illustrated in a frequency space is shown in FIG. 5B. In FIG. 5B, the abscissa denotes the frequency of the image in the X direction and the ordinate denotes the frequency of the image in the Y direction. In a position of the 16th pixel in the Y direction from the center of the image indicated in FIG. 5B, a high luminance line appears that corresponds to a change in the 32-pixel period. This enables a second period to be evaluated in correspondence to the relationship between the change period=512/partitioned number of FIG. 5A and the high luminance line position=512/(change period of FIG. 5A) of FIG. 5B.

Here, high luminance lines appearing in the second period, that is a part of 16th pixel or above in the Y direction illustrated in FIG. 5B are frequency lines included because the luminance change of FIG. 5A is schematized by rectangular changes. In this manner, a scanning method renders it possible to estimate the frequency of a change appearing on an image (hereinafter, referred to as an "artifact"). From this result, the inventor has given thought that artifacts on an image can be decreased by the elimination of a frequency part corresponding to an artifact by an image processing.

Figure 6A:
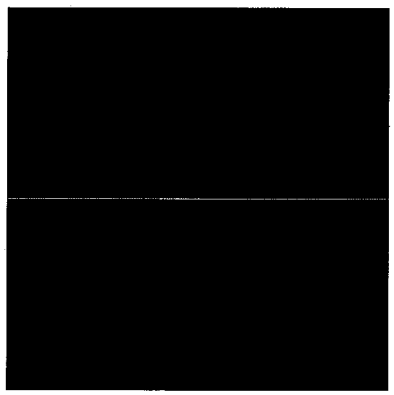
FIG. 6A shows a 0 filling image example in which a frequency part corresponding to an artifact is removed.

FIG. 6A is a diagram indicating an example of an image in which a frequency part in a Fourier transformed image indicated in FIG. 5B is removed corresponding to an artifact by an image processing. The image is so-called 0 filling image, which is a Fourier transformed image obtained with the elimination of a frequency component corresponding to an artifact by 0 filling processing. Here is a simple description of image processing. A scanning method shows in advance the presence of a signal corresponding to an artifact in a 16th pixel position from the center in the Y direction, so the signal of its position is replaced by "0" by image processing. In addition, a frequency position of a signal corresponding to an artifact can be determined by a scanning method, however, the distribution condition around a main frequency differs depending on intensity conditions of signals. Therefore, the vertical and horizontal widths to be replaced by "0" and to be removed are preferably determined in advance by an experiment or the like. Additionally, another option is devised where the signal of its surrounding luminance changes to be replaced by "0" gradually, without complete replacement by "0".

Figure 6B:
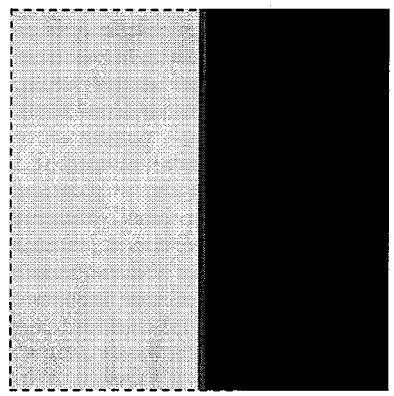
FIG. 6B is an image example in which an artifact obtained by its inverse Fourier transformation is decreased.

FIG. 6B shows an image where a frequency space image indicated in FIG. 6A is inverse Fourier-transformed. The inverse Fourier-transformed image indicated in FIG. 6B shows that a changing part indicated in FIG. 5A is filtered, so that the changes become smooth.

Figure 7:
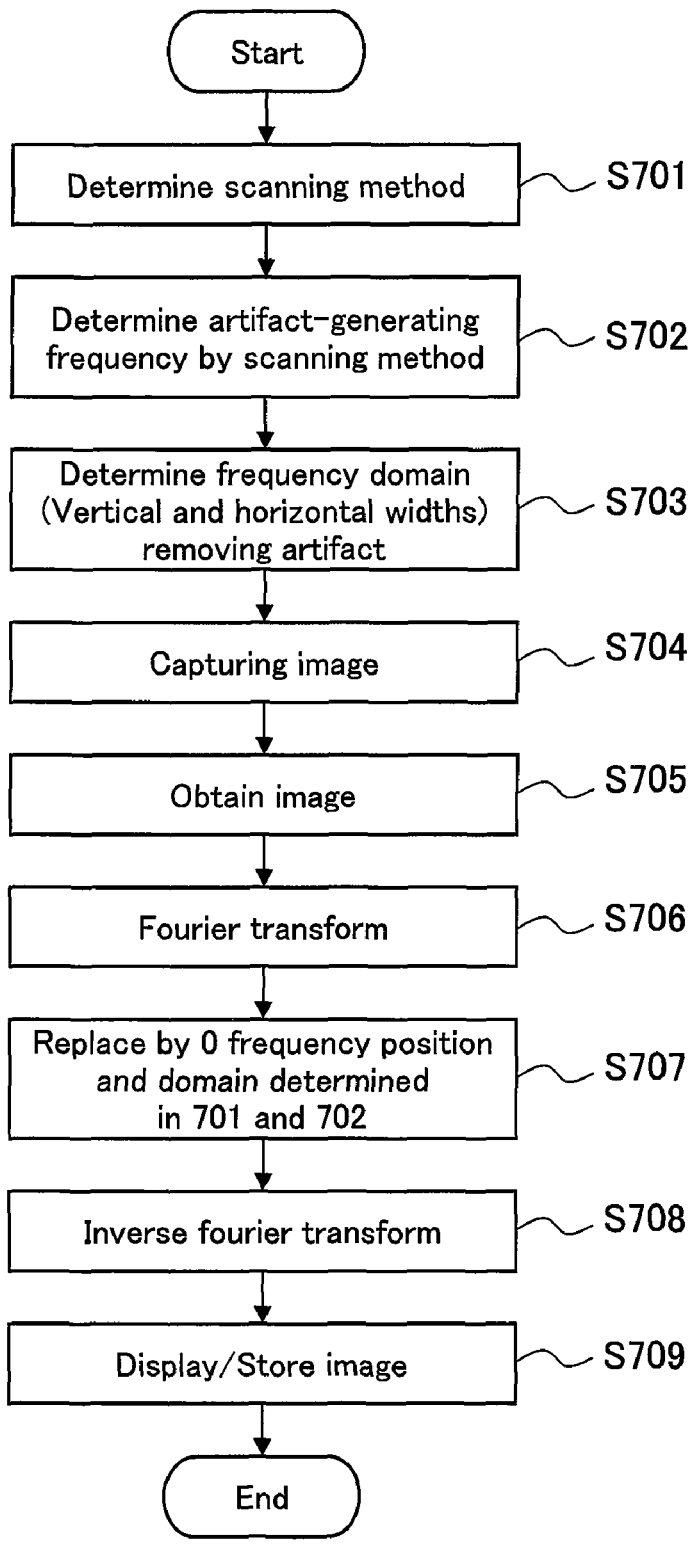
FIG. 7 shows a flowchart indicating an image processing flow according to the present embodiment.

FIG. 7 shows a flowchart indicating a processing flow for implementation of an image transformation in a scanning electron microscope according to the present embodiment. Firstly, in a step 701, the scanning method is determined. In a step 702, according to the scanning method determined in the step 701, the frequency of an artifact appearing on an image can be determined on the basis of the relation depicted with reference to FIGS. 5A and 5B. In a step 703, a frequency domain for removing an artifact is determined based on the vertical and horizontal widths determined by an experiment or the like in advance with respect to the frequency position of the step 702. In steps 704 and 705, an image is obtained after the image capturing. An image thus obtained is Fourier transformed in a step 706 and then the frequency domain thus determined in the step 703 is replaced, for example, by "0." Its image is inverse Fourier-transformed in a step 708 and the image is displayed and stored in a step 709. The flow of such processing renders it possible to decrease an artifact which appears on an image depending on a scanning method.

Note that a frequency domain (vertical and horizontal widths) determined in the step 703 and a method for replacement by "0" in the step 707 can be determined, in advance depending on the kind of inspected samples. The replacement method can also be employed among several methods depending on the kind of the samples.

Figure 8:
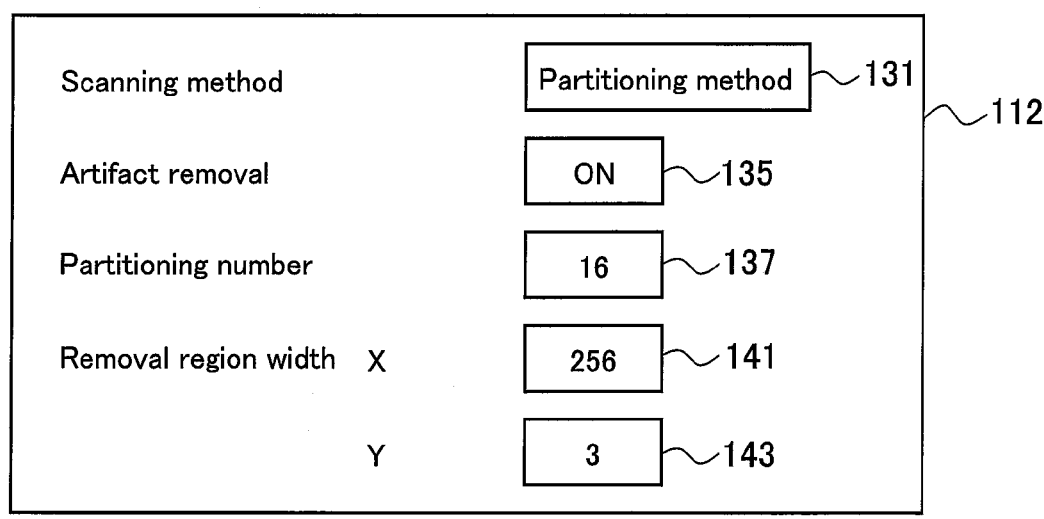
FIG. 8 shows an operation screen example of a scanning electron microscope according to the present embodiment and is a diagram indicating an operation setting screen example relating to artifact processing.

FIG. 8 is a diagram indicating an example of operation screen when an operator selectively carries out artifact removal processing following a scanning method according to the present embodiment. The constitution of this scanning screen may display a menu for example, or each item may be set in a hardware manner. An operation screen 112 includes an input region of the following items: a scanning method 131; ON/OFF options 135 for artifact removal processing; a number of partitioned region 137; a region removal width 141 in the X direction; and a region removal width 143 in the Y direction. Here, the scanning method 131 is inputted and then one of the ON/OFF options 135 for artifact removal is selected. In case ON is selected, the number of image partitions for the scanning method and the vertical and horizontal widths of a frequency domain to be removed are inputted. A region removal width X is generally the entire width of a screen in the lateral direction. Here, a region removal width Y is particularly important. For example, if the value 3 is insufficient for artifact removal, an appropriate value can be determined by viewing the screen while increasing the value to 4 to 5 upward.

According to the present embodiment, the advantages as described below are offered.

That is, conventionally, a scanning method devised to decrease the influence of charge between scan lines creates a problem that an artifact is generated on an image. For the solution of this problem, the frequency of an artifact generated attributable to a scanning method is evaluated in advance according to the scanning method, and then the image component in the frequency domain corresponding to the frequency of an artifact is removed to be thereby capable of obtaining a fine image in which the influence of the artifact is decreased.

The present invention is applicable to a charged particle beam apparatus.

EXPLANATION OF REFERENCE NUMERALS

101 ... SAMPLE STAGE
102 ... SAMPLE
103 ... DETECTOR
104 ... CATHODE
105 ... SCANNING COIL
106 ... ELECTRON LENS
107 ... A/D CONVERTER
108 ... SCANNING COIL CONTROLLING CIRCUIT
109 ... LENS CONTROLLING CIRCUIT
110 ... IMAGE PROCESSOR
111 ... CONTROLLING CALCULATOR
112 ... DISPLAY DEVICE
113 ... INPUT MEANS
114 ... ELECTRON BEAM

What is claimed is:

1. A charged particle beam apparatus comprising:
a scanning section that scans a sample two-dimensionally, in first and second directions, with a charged particle beam so as to display an image of the scanned region with a signal based on a charged particle beam from the sample detected by the scanning, wherein the scanning section employs a partitioning and interlacing method in which a plurality of partitioned regions are defined by partitioning a region to be scanned, in the second direction, that is different from the first direction, and scanning in the first direction is performed for every partitioned region sequentially in a skipping manner; and,
an image processing section for removing an artifact that is attributable to the scanning;
wherein the image processing section removes the artifact by a processing based on a frequency of the artifact that is pre-evaluated according to the size of the partitioned region in the second direction.

2. The charged particle beam apparatus according to claim 1, wherein
the image processing section removes the artifact appearing in a Fourier transformed image obtained by Fourier transforming an actual image.

3. The charged particle beam apparatus according to claim 1, wherein:
when i) a first period is a number of pixels in each partitioned regions, which number is obtained by dividing the number of pixels in the second direction in an actual image by the number of partitioned regions, and ii) a frequency image is a Fourier transformed image that corresponds to the first period, and is obtained by Fourier transforming the actual image, the image processing section carries out a process of removing a luminance signal of the frequency image at multiple frequencies;
the luminance signals are arranged in the first direction; and
the luminance signals result from Fourier transformation of an image that corresponds to the first period.

4. The charged particle beam apparatus according to claim 1, wherein when i) a first period is a number of pixels in each partitioned regions, which number is obtained by dividing the number of pixels in the second direction in an actual image by the number of the partitioned regions, and ii) a frequency image is a Fourier transformed image that corresponds to the first period, and is obtained by Fourier transforming the actual image, the image processing section carries out a process of replacing a luminance signal of the frequency image with a background value on pixels arranged in the first direction at a second frequency after the Fourier transformation and corresponding to the first period.

5. The charged particle beam apparatus according to claim 1, further comprising a user interface for changeably setting the number of partitioned regions and an artifact removing region at least in the second direction.

6. The charged particle beam apparatus according to claim 1, further comprising:
a Fourier transforming section that Fourier transforms an actual image data; and
an inverse Fourier transforming section that subjects a frequency image to inverse Fourier transformation.

7. A method of operating
a charged particle beam apparatus, the method comprising:
scanning a sample two-dimensionally, in first and second directions, with a charged particle beam so as to display an image of the scanned region with a signal based on a charged particle beam from the sample detected by the scanning, wherein the scanning employs a partitioning and interlacing method in which scanning in the first direction is performed for partitioned regions sequentially in a skipping manner;
defining the partitioned regions by partitioning a region to be scanned, in the second direction that is different from the first direction, into a plurality of regions; and
carrying out image processing for removing an artifact that is attributable to the scanning; wherein the artifact is removed by a processing based on a frequency of the artifact that is pre-evaluated according to the size of the partitioned regions in the second direction.

* * * * *